United States Patent
Wu et al.

(10) Patent No.: US 6,891,065 B2
(45) Date of Patent: May 10, 2005

(54) ADVANCED ROUTE FOR THE SYNTHESIS OF CPLA₂ INHIBITORS

(75) Inventors: Yanzhong Wu, Bronx, NY (US); Panolil Raveendranath, Monroe, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/896,318

(22) Filed: Jul. 21, 2004

(65) Prior Publication Data

US 2005/0020858 A1 Jan. 27, 2005

Related U.S. Application Data

(60) Provisional application No. 60/490,005, filed on Jul. 25, 2003.

(51) Int. Cl.⁷ .................... C07D 209/04; C07C 255/58; C07C 303/40; C07C 311/13; C07C 295/59
(52) U.S. Cl. .................. 564/99; 548/506; 548/507; 558/413; 564/89; 564/92; 564/97
(58) Field of Search ................. 548/506, 507; 558/413; 564/89, 92, 97, 99

(56) References Cited

U.S. PATENT DOCUMENTS

| | | | |
|---|---|---|---|
| 6,635,771 B2 | 10/2003 | McKew et al. | |
| 6,797,708 B2 * | 9/2004 | McKew et al. | .......... 514/228.2 |
| 6,812,252 B2 * | 11/2004 | Ikawa et al. | ................. 514/603 |
| 2003/0144282 A1 | 7/2003 | McKew et al. | |

FOREIGN PATENT DOCUMENTS

WO WO 03/048122 A2 6/2003

OTHER PUBLICATIONS

Fagnola et al., Solid–Phase Synthesis of Indoles Using the Palladium–Catalysed Coupling of Alkynes with Iodoaniline Derivatives, *Tetrahedron Letters*, (1997), vol. 38, No. 13, pp 2307–2310.

Appleton et al., A Mild and Selective C–3 Reductive Alkylation of Indoles, *Terahedron Letters*, (1993), vol. 34, No. 9, pp. 1529–1532.

B.M. Nilsson, et al: "Derivatives of the muscarinic agent N–methyl–N–(1–methyl–4–pyrrolidino–2–butynyl)acetamide" Journal of Medicinal Chemistry, vol. 31, No. 3, Mar. 1988 pp. 577–582.

J. Fujiwara, et al: "Nucleophilic aromatic substitution by organoaluminum reagents. Application to the synthesis of indoles" Journal of the American Chemical Society, vol. 105, No. 24, Nov. 16, 1983 pp. 7177–1779.

Database Caplus Chemical Abstracts Service, Columbus, Ohio, US; database accession No. 1990–532816.

Jianping Deng, et al: Synthesis and characterization of poly(N–propargylsulphamides) Macromolecules, vol. 37, No. 15, Jun. 25, 2004, pp. 5538–5543.

International Search Report for International application No. PCT/US2004/023247.

* cited by examiner

*Primary Examiner*—Peter O'Sullivan

(57) ABSTRACT

A process for making a compound of formula (I)

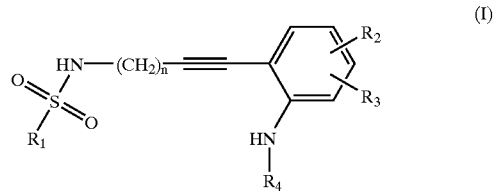

in which process the compound $HC{\equiv}C{-}(CH_2)_n{-}NH_2$ is reacted with the compound $R_1{-}SO_2Cl$ to produce an intermediate compound, which intermediate compound is then reacted with the compound of formula

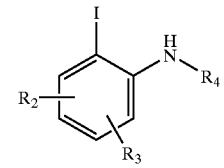

to produce the compound of formula (I), and compounds produced by the process of this invention. The terms $R_1$, $R_2$, $R_3$, $R_4$ and n have the definitions set forth in the specification.

20 Claims, No Drawings

ADVANCED ROUTE FOR THE SYNTHESIS OF CPLA$_2$ INHIBITORS

This application claims priority from copending provisional application(s) No. 60/490,005 filed on Jul. 25, 2003.

FIELD OF THE INVENTION

This invention relates to the preparation of inhibitors of the enzyme cytosolic phospholipase A$_2$ (cPLA$_2$).

BACKGROUND OF THE INVENTION

Compounds which inhibit cytosolic phospholipase A$_2$ and a process for making those compounds have been disclosed in U.S. Patent Publication No. 2003-0144282 A1, filed Nov. 22, 2002, the disclosure of which is incorporated by reference herein. These compounds are useful for a variety of purposes, including the relief of pain and inflammation. In order to bring a drug to market, it is necessary to have an economically feasible process for making the compound. Often, a process that works in the laboratory is not practical from a commercial standpoint. It would be desirable to have a relatively inexpensive and efficient method for making at least some of the aforesaid compounds.

Appleton, et al., in *Tetrahedron Lett.* 1993, 34, 1529, teach reductive C-3 alkylation of 3-unsubstituted indoles to produce C-3 functionalized indoles, especially 3-(arylmethyl)indoles and 3-(heteroarylmethyl)indoles. In the reference reaction, the initial indole is reacted with an aldehyde or ketone using triethylsilane and trifluoroacetic acid.

A solid-phase synthesis of indoles using palladium-catalyzed coupling of alkynes with iodoaniline derivatives is described by Fagnola, et al., *Tetrahedron Letters*, 38(13), 2307–2310 (1997).

SUMMARY OF THE INVENTION

The present invention comprises a process for making a compound of formula (I)

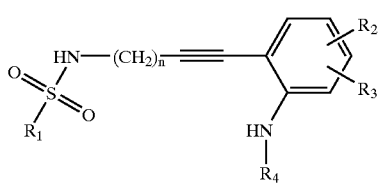
(I)

wherein:
n is an integer in the range of 0–10;
R$_1$ represents a straight or branched C$_1$–C$_{10}$ alkyl group, or —CH$_2$-phenyl wherein the phenyl ring optionally has up to two substituents independently selected from the group consisting of C$_1$–C$_4$ alkyl, C$_1$–C$_4$ alkoxy, halogen, and nitrile, each alkyl and alkoxy being optionally substituted by from one to the maximum number of halogen atoms;
R$_2$ and R$_3$ are each independently selected from the group consisting of H, halogen, nitrile, C$_1$–C$_4$ alkyl, and C$_1$–C$_4$ alkoxy; and R$_4$ represents a straight or branched C$_1$–C$_{10}$-alkyl group,

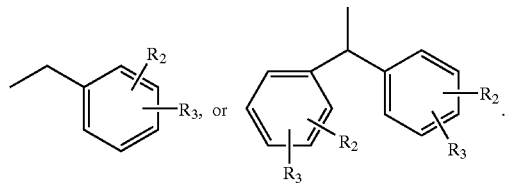

The process comprises reacting the compound HC≡C—(CH$_2$)$_n$—NH$_2$ where n represents an integer from 0–10, or a salt form thereof, preferably an HCl salt thereof, under mildly alkaline conditions, preferably in a solution of potassium carbonate, with the compound R$_1$—SO$_2$Cl to produce the intermediate compound of formula (II)

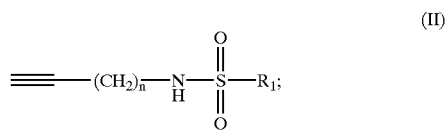
(II)

and then reacting the compound of formula (II) with the compound of formula

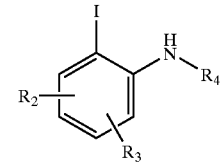

preferably in the presence of a catalyst.

The compound of formula (I) may be cyclized by heating, preferably in NMP in the presence of a catalytic amount of CuI, to form a compound of formula (III)

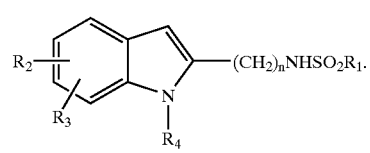
(III)

The compound of formula (III) may be reacted with a compound of formula O═CH—R$_5$ in the presence of a reducing agent under acidic conditions, where R$_5$ is —(CH$_2$)$_m$—X-phenyl-C(O)OR$_6$, m is an integer in the range of 1–4, X is O or CH$_2$, and R$_6$ is C$_1$–C$_4$ alkyl, to form a compound of formula (IV)

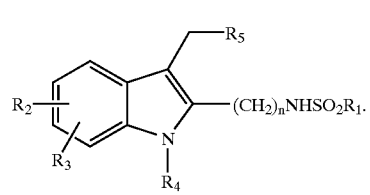
(IV)

The compound of formula (IV) may be reacted with LiOH in THF, methanol and water to convert R$_5$ to R$_7$, where R$_7$ is —(CH$_2$)$_m$—X-phenyl-C(O)OH.

The present invention further comprises compounds of formulae (I) and (II).

Various advantages and objects of the present invention will be apparent to those skilled in the art from the description below and from the appended claims.

DETAILED DESCRIPTION OF THE PREFERRED EMBODIMENTS

This invention provides a novel process for making various compounds in the synthesis of a class of substituted indoles which are useful as inhibitors of cPLA$_2$. These cPLA$_2$ inhibitors include, for example, 4-[3-[5-chloro-2-[2-[[[(3,4-dichlorophenyl)-methyl]-sulfonyl]amino]ethyl]-1-(diphenylmethyl)-1H-indol-3-yl]propyl]benzoic acid and 4-[2-[5-chloro-2-[2-[[[(3,4-dichlorophenyl)methyl]-sulfonyl]amino]ethyl]-1-(diphenylmethyl)-1H-indol-3-yl]ethoxy]benzoic acid, as well as many other compounds. They are useful for relieving pain and inflammation associated with a variety of conditions or disease states.

In the process of this invention, n may be an integer in the range of 0–10, but is preferably 0–4 and most preferably is 1, 2, or 3. R$_1$ is preferably —CH$_2$-phenyl, wherein the phenyl ring optionally has up to two substituents independently selected from the group consisting of C$_1$–C$_4$ alkyl, C$_1$–C$_4$ alkoxy, halogen, and nitrile, each alkyl and alkoxy group being optionally substituted by from one to the maximum number of halogen atoms. More preferably, the substituents are halogen, alkyl or perfluoroalkyl. Especially preferred R$_1$ groups include 3,4-dichlorophenylmethyl, 2,6-dimethylphenylmethyl and 2-(trifluoromethyl)phenylmethyl. R$_2$ and R$_3$ are preferably H, F, Cl, or Br. R$_4$ is preferably a benzhydryl group, especially an unsubstituted benzhydryl group. Preferably, R$_6$ is methyl or ethyl and m is 2. Examples of highly preferred R$_5$ groups include —(CH$_2$)$_2$—O-(p-)phenyl-C(O)OCH$_3$ and —(CH$_2$)$_3$-(p-)phenyl-C(O)OC$_2$H$_5$.

In the reaction of the alkynylamine and the sulfonylchloride to form a compound of formula (II), it is highly preferred to use a solution of K$_2$CO$_3$ in THF and water. However, other suitable bases or solvents may be used. Those skilled in the art will readily be able to determine which solutions are suitable in carrying out this reaction.

In reacting the compound of formula (II) with the substituted 2-iodophenylamine compound, a suitable catalyst is preferably employed. Preferably, the catalyst is CuI and/or dichlorobis(triphenylphosphine)palladium (II). It is preferable to carry out the reaction in a solvent such as THF, or the like.

In one preferred aspect of the invention, the compound of formula (I) may be converted to a compound of formula (III) by heating, preferably in the presence of a catalyst such as CuI in a solvent such as N-methylpyrrolidinone. Other suitable catalysts and/or solvents known to those skilled in the art may also be employed. The compound of formula (I) suitably may be heated to approximately 100–140° C., preferably to about 120° C., until the conversion to an indole compound is completed.

In a further aspect of the invention, the compound of formula (III) is reacted with an aldehyde of formula R$_5$CHO in the presence of a reducing agent to make a compound of formula (IV). Preferably, this reaction takes place in an acidic solvent system. Suitable solvent systems include mixtures of a halogenated acid such as chloroacetic acid, di or trichloroacetic acid, trifluoroacetic acid and/or a Lewis acid such as boron trifluoride and dichloromethane, preferably with trifluoroacetic acid. Suitable reducing agents include triethylsilane, or the like. Those skilled in the art will readily be able to identify other suitable solvent systems and reducing agents to use in the practice of this invention.

The compound of formula (IV) may be converted from an ester to an acid by any means known in the art. A preferred method is to react the ester with LiOH in THF, methanol and water to produce a compound of formula (V)

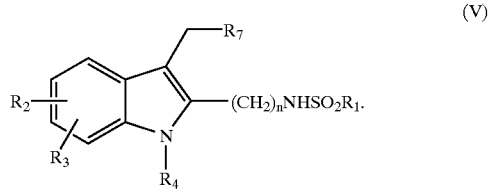

This invention provides a method for making a wide variety of C-2 and C-3 substituted indole compounds, such as compounds of formulae (III), (IV) and (V), shown above. Scheme 1 illustrates various preferred aspects of this invention. In Scheme 1 below, the terms n, R$_1$, R$_2$, R$_3$, R$_4$, R$_5$ and R$_7$ have the definitions set forth above, THF refers to tetrahydrofuran, NMP refers to N-methylpyrrolidinone and TFA refers to trifluoroacetic acid.

Scheme 1

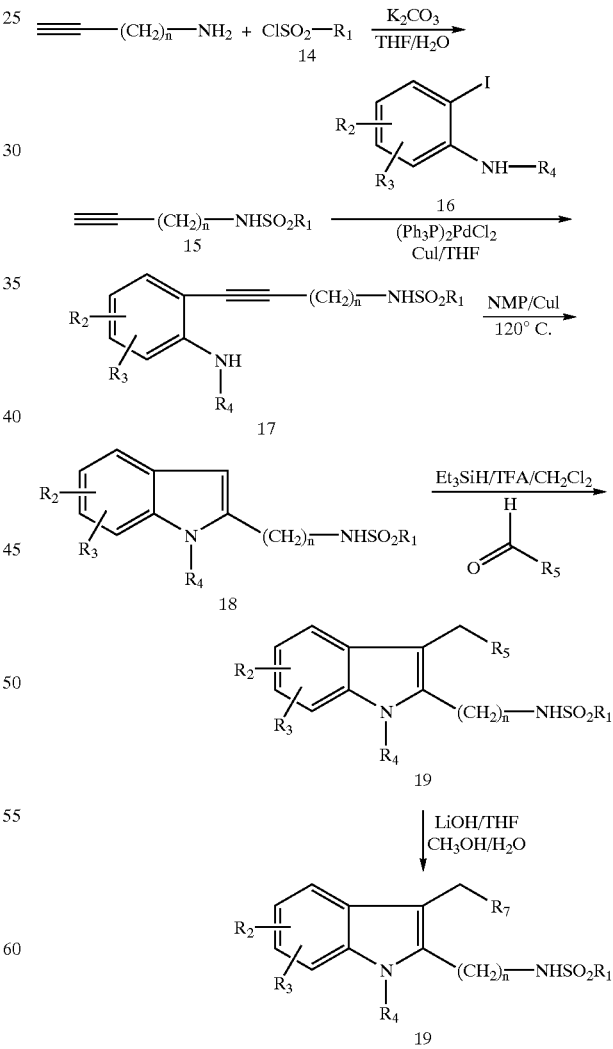

Scheme 2 illustrates a highly preferred embodiment of the present invention, providing a relatively short synthesis for 4-[3-[5-chloro-2-[2-[[[(3,4-dichlorophenyl)-methyl]-sulfonyl]amino]ethyl]-1-(diphenylmethyl)-1H-indol-3-yl]propyl]benzoic acid (2) and 4-[2-[5-chloro-2-[2-[[[(3,4-dichlorophenyl)methyl]sulfonyl]-amino]ethyl]-1-(diphenylmethyl)-1H-indol-3-yl]ethoxy]benzoic acid (3).

(II) to give an arylalkyne derivative. Cyclization of this arylalkyne is performed in N-methyl-pyrrolidinone with catalytic amount of CuI to give corresponding indole (9) in two steps. These coupling and cyclization reactions are known as Sonogashira and Castro reactions and are medi-

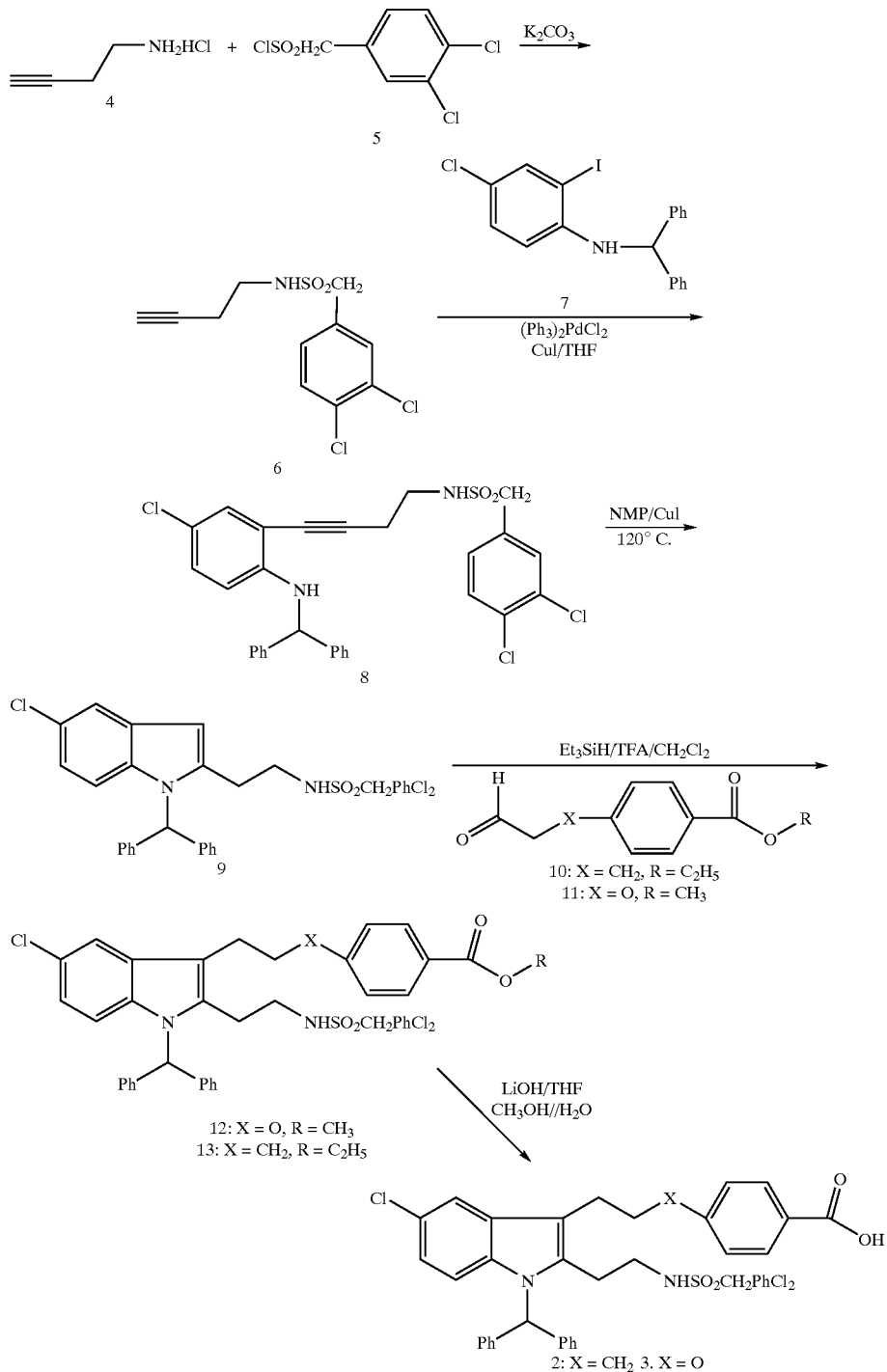

In Scheme 2, the first intermediate (6) is coupled with benzhydryl-(4-chloro-2-iodophenyl)amine (7) with a catalytic amount of dichlorobis(triphenylphosphine) palladium ated by catalytic palladium and copper salts. The indole (9) can be alkylated with the aldehyde (10) using the reagent combination triethylsilane and trifluoroacetic acid in dichloromethane to yield the ester (13). Compound (12) is produced when the indole (9) is alkylated with the aldehyde (11) under the same conditions, but the yield typically is smaller. Hydrolysis of the ester (13) under common basic conditions produces the compound (2), and the ester (12) may be hydrolyzed to produce the compound (3).

Other highly preferred embodiments of the present invention include a process comprising the reactions illustrated in Scheme 2 wherein in compounds 8, 10–13, and 2–3 in place of the 3,4-dichlorophenyl group is a 2,6-dimethylphenyl or 2-(trifluoromethyl)phenyl group.

The present invention provides a variety of new compounds. Examples of these new compounds include:
N-But-3-ynyl-1-(3,4-dichlorophenyl)methanesulfonamide,
N-{4-[2-(benzhydrylamino)-5-chlorophenyl]but-3-ynyl}-1-(3,4-dichlorophenyl)-methanesulfonamide,
N-[2-(1-benzhydryl-5-chloro-1H-indol-2-yl)ethyl]-1-(3,4-dichlorophenyl)methanesulfonamide, and
ethyl 4-{3-[1-benzhydryl-5-chloro-2-(2-{[(3,4-dichlorobenzyl)sulfonyl]amino}ethyl)-1H-indol-3-yl]propyl}benzoate.

Other examples include:
N-But-3-ynyl-1-(2,6-dimethylphenyl)methanesulfonamide,
N-{4-[2-(benzhydrylamino)$_5$-chlorophenyl]but-3-ynyl}1-(2,6-dimethylphenyl)methanesulfonamide,
N-[2-(1-benzhydryl-5-chloro-1H-indol-2-yl)ethyl]-1-(2,6-dimethylphenyl)methane-sulfonamide,
ethyl 4-{3-[1-benzhydryl-5-chloro-2-(2-{[(2,6-dimethylbenzyl)sulfonyl]amino}ethyl)-1H-indol-3-yl]propyl}benzoate,
N-But-3-ynyl-1-(2-(trifluoromethyl)phenyl)methanesulfonamide,
N-{4-[2-(benzhydrylamino)-5-chlorophenyl]but-3-ynyl}1-(2-(trifluoromethyl)phenyl)-methanesulfonamide,
N-[2-(1-benzhydryl-5-chloro-1H-indol-2-yl)ethyl]-1-(2-(trifluoromethyl)phenyl)-methane-sulfonamide, and
ethyl 4-{3-[1-benzhydryl-5-chloro-2-(2-{[(2-(trifluoromethyl)benzyl)sulfonyl]amino}-ethyl)-1H-indol-3-yl]propyl}benzoate.

Unless the context dictates otherwise, the following terms have the meanings set forth below wherever they appear in this specification or the appended claims.

Halogen and halo- refer to F, Cl, Br and I. Alkyl refers to a saturated hydrocarbon substituent or group containing from one to twenty carbon atoms and having straight or branched chains. Alkenyl refers to a hydrocarbon substituent or group containing from one to twenty carbon atoms, at least one carbon—carbon double bond, and having straight or branched chains. Alkynyl refers to a hydrocarbon substituent or group containing from one to twenty carbon atoms, at least one carbon—carbon triple bond, and having straight or branched chains. Alkoxy refers to an alkyl group bonded to an oxygen atom by a single oxygen-carbon bond. Aryl refers to an unsaturated hydrocarbon ring system containing from one to three fused rings, in which each ring is composed of 5–7 atoms and has conjugated double bonds. Heteroaryl refers to an unsaturated ring system which differs form aryl in that at least one ring atom is nitrogen, oxygen or sulfur.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

Salts may also be formed from organic and inorganic bases, preferably alkali metal salts, for example, sodium, lithium, or potassium, when a compound of this invention contains an acidic moiety.

Pharmaceutically acceptable esters can be formed from reaction with an alcohol, for example, a $C_1$–$C_6$ alkanol, when a compound of this invention contains an acidic moiety.

The following examples are presented to illustrate certain embodiments of the present invention, but should not be construed as limiting the scope of this invention.

EXAMPLE 1

N-But-3-ynyl-1-(3,4-dichlorophenyl)methanesulfonamide

To a mixture of potassium carbonate (40.2 g, 296 mmol) in water (50 mL) and THF (50 mL) at 15–20° C. was added but-3-ynylamine hydrogen chloride (10.4 g, 98.5 mmol). Then, (3,4-dichlorophenyl)methanesulfonyl chloride (5, 30.7 g, 118 mmol) was added in portions during of a period of 30 ml. The mixture was stirred for 4 h at rt. THF is evaporated. The mixture is extracted with EtOAc (2×200 mL). The combined organic extracts were dried over $Na_4SO_4$. The solvent is evaporated to give a white solid (20.5 g, 71%%). $^1H$ NMR ($CDCl_3$): δ7.53 (d, 1H, J=2.0 Hz), 7.47 (d, 1H, J=4.2 Hz), 7.27 (m, 1H), 4.52 (t, 1H, J=6.2 Hz), 4.22 (s, 2H), 3.17 (dd, 2H, J=6.2 Hz, 12.5 Hz), 2.41 (m, 2H), 2.07 (m, 1H)

EXAMPLE 2

N-{4-[2-(benzhydrylamino)-5-chlorophenyl]but-3-ynyl}-1-(3,4-dichlorophenyl)-methanesulfonamide To a mixture of benzhydryl-(4-chloro-2-iodophenyl)amine (2.0 g, 4.76 mmol), dichlorobis(triphenylphosphine) palladium (II) (66.8 mg, 0.0952 mmol), copper (I) iodide (18.0 mg, 0.0952 mmol), and triethylamine (0.72 g, 7.14 mmol) was added N-but-3-ynyl-1-(3,4-dichlorophenyl) methanesulfonamide__(1.67 g, 5.71 mmol). The mixture was stirred for 18 h at rt. Then, N-but-3-ynyl-1-(3,4-dichlorophenyl)methanesulfonamide__(0.42 g) was added. The mixture was stirred for 3 hours. The solvent was evaporated. The residue was purified by column chromatography, using a mixture of heptane and EtOAc (3:1) as elute to give a white solid (2.20 g, 81%). $^1H$ NMR ($CDCl_3$): δ7.2–7.6 (m, Ph, $CHPh_2$), 6.98 (m, 1H), 6.30 (d, 1H, J=8.9 Hz), 5.49 (d, 1H, J=4.6 Hz), 5.06 (d, 1H, J=4.5 Hz), 4.38 (t, 1H, J=6.24 Hz), 4.14 (s, 2H), 3.14 (dd, 2H, J=6.4, 12.6 Hz), 2.61 (t, 2H, J=6.3 Hz).

EXAMPLE 3

N-[2-(1-benzhydryl-5-chloro-1H-indol-2-yl)ethyl]-1-(3,4-dichlorophenyl)methanesulfonamide A mixture of N-{4-[2-(benzhydrylamino)-5-chlorophenyl]but-3-ynyl}-1-(3,4-dichlorophenyl)-methanesulfonamide (1.0 g, 1.71 mmol) and copper (I) iodide (0.30 g, 1.58 mmol) was heated to 120° C. and stirred for 7 h, and then cooled to room temperature. Water (50 mL) was added. The mixture was extracted with EtOAc (2×50 mL). The combined organic extracts were dried over $Na_2SO_4$. The solvent was evaporated. The residue was purified by column chromatography, using a mixture of heptane and EtOAc (2:1) as elute to give a white solid (0.76 g, 76%). $^1H$ NMR ($CDCl_3$): δ6.7–7.6 (m, Ph. $CHPh_2$), 6.58 (d, 1H, J=8.9 Hz), 4.20 (m, 1H), 3.99 (s, 2H), 3.10 (dd, 2H, J=6.9, 13.3 Hz), 2.94 (t, 2H, J=6.7 Hz).

EXAMPLE 4

Ethyl 4-{3-[1-benzhydryl-5-chloro-2-(2-{[(3,4-dichlorobenzyl)sulfonyl]amino}ethyl)-1H-indol-3-yl]propyl}benzoate To a solution N-[2-(1-benzhydryl-5-chloro-1H-indol-2-yl)ethyl]-1-(3,4-dichlorophenyl)-methanesulfonamide (3.0 g, 5.14 mmol), triethylsilane (1.79 g, 15.4 mmol), and 4-(3-oxopropyl)benzoic acid ethyl ester (1.26 g, 6.16 mmol) in dichloromethane (30 mL) at −20 to −25° C. was added trifloroacetic acid (2.93 g, 25.7 mmol) during a period of 1 min. The mixture was warmed to −10° C. and stirred for 4 h. Saturated aqueous NaHCO$_3$ (20 mL) was added. The mixture was extracted with EtOAc (150 mL). The organic extract was dried over Na$_2$SO$_4$. The solvent is evaporated. The residue is purified by column chromatography, using a mixture of heptane and EtOAc (4:1) as elute to give a white solid (2.25 g, 56%). $^1$H NMR (CDCl$_3$): δ6.9–7.6 (m, Ph, CHPh$_2$), 7.97 (d, 1H, J=1.6 Hz), 7.41 (d, 1H, J=1.9 Hz), 6.50 (d, 1H, J=8.9 Hz), 4.35 (dd, 2H, J=7.1, 14.3 Hz), 4.13 (m, 1H), 3.92 (s, 2H), 2.95 (m, 2H), 2.71 (m, 6H), 1.96 (m, 2H), 1.38 (t, 3H, J=7.1 Hz).

EXAMPLE 5

4-[3-[5-chloro-2-[2-[[[(3,4-dichlorophenyl)-methyl]-sulfonyl]amino]ethyl]-1-(diphenylmethyl)-1H-indol-3-yl]propyl] Benzoic Acid A solution of ethyl 4-{3-[1-benzhydryl-5-chloro-2-(2-{[(3,4-dichlorobenzyl)sulfonyl]-amino}ethyl)-1H-indol-3-yl]propyl}benzoate (0.50 g, 0.65 mmol), LiOH (0.24 g, 10.0 mmol), methanol (5 mL), THF (5 mL) and water (5 mL) was stirred for 18 h at rt, then diluted with water (200 mL). 1 N HCl (10 mL) was added. The reaction mixture was extracted with EtOAc (2×50 mL). The organic extracts were dried over Na$_2$SO$_4$. The solvent is evaporated to give a white solid (0.46 g, 96%). $^1$H NMR (DMSO$_{d6}$): 512.80 (br.s, 1H), 7.89 (d, 2H, J=2 Hz), 7.59 (d, 1H, J=1.5 Hz), 7.53 (d, 1H, J=6 Hz), 7.48 (d, 1H, J=1.5 Hz), 7.38 (m, 9H), 7.20 (m, 5H), 6.77 (dd, 1H, J=6.9 & 1.5 Hz), 6.46 (d, 1H, J=6.9 Hz), 4.36 (s, 2H), 3.18 (m, 2H), 2.96 (m, 2H), 2.76 (m, 4H), 1.90 (m, 2H).

Many variations of the present invention not illustrated herein will occur to those skilled in the art. The present invention is not limited to the embodiments illustrated and described herein, but encompasses all the subject matter within the scope of the appended claims.

What is claimed is:

1. A process for making a compound of formula (I)

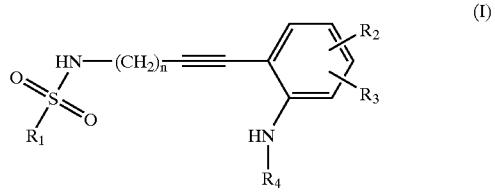

(I)

wherein:
n is an integer in the range of 0–10;
R$_1$ represents a straight or branched C$_1$–C$_{10}$alkyl group or —CH$_2$-phenyl wherein the phenyl optionally has up to two substituents independently selected from the group consisting of C$_1$–C$_4$alkyl, C$_1$–C$_4$alkoxy, halogen, and nitrile, each alkyl and alkoxy being optionally substituted by from one to the maximum number of halogen atoms; R$_2$ and R$_3$ are each independently selected from the group consisting of H, halogen, nitrile, C$_1$–C$_4$alkyl, and C$_1$–C$_4$alkoxy; and R$_4$ represents a straight or branched C$_1$–C$_{10}$alkyl group,

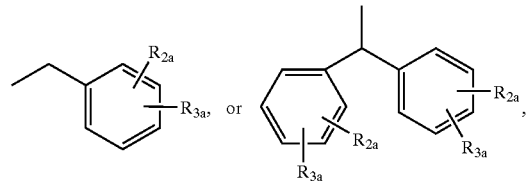

wherein R$_{2a}$, and R$_{3a}$ are each independently selected from the group consisting of H, halogen, nitrile, C$_1$–C$_4$alkyl, and C$_1$–C$_4$alkoxy, said process comprising:
a) reacting the compound R$_1$—SO$_2$Cl with the compound HC≡C—(CH$_2$)$_n$—NH$_2$ or a salt form thereof, where n represents an integer from 0–10, under alkaline conditions to produce the intermediate compound of formula (II)

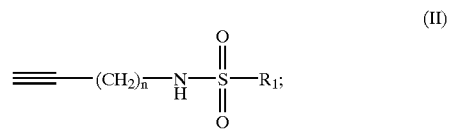

(II)

and then;
b) reacting the compound of formula (II) with the compound of formula

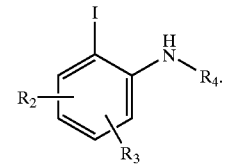

2. The process of claim 1 wherein reaction step a) is performed in a potassium carbonate solution, and reaction step b) is performed in the presence of a catalyst.

3. The process of claim 2 wherein the catalyst comprises copper (I) iodide, dichlorobis(triphenylphosphine)palladium (II), or a combination thereof.

4. The process of claim 1 wherein R$_4$ is a benzhydryl group.

5. The process of claim 1 wherein R$_1$ represents —CH$_2$-phenyl wherein the phenyl is optionally substituted by up to two halogen, or optionally halogenated C$_1$–C$_4$alkyl or C$_1$–C$_4$alkoxy substituents.

6. The process of claim 5 wherein n is 1, 2 or 3.

7. The process of claim 6 wherein: in R$_1$, the phenyl is optionally substituted by up to two halogen, methyl or trifluoromethyl substituents; R$_2$ is H; R$_3$ is Cl; and R$_4$ is an unsubstituted benzhydryl group.

8. The process of claim 7 wherein step a) is performed in a solution of K$_2$CO$_3$ in tetrahydrofuran and water, and step b) is performed in tetrahydrofuran in the presence of CuI and dichlorobis(triphenylphosphine)palladium (II).

9. The process of claim 1 further comprising heating the compound of formula (I) to produce an indole compound of formula (III)

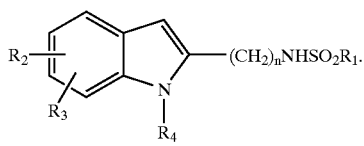
(III)

10. The process of claim 9 wherein the compound of formula (I) is heated to a temperature in the approximate range of 100–140° C. in N-methylpyrrolidinone in the presence of CuI.

11. The process of claim 9 further comprising reacting the compound of formula (III) with an aldehyde compound of formula $R_5CHO$ in the presence of a reducing agent under acidic conditions, where $R_5$ represents —$(CH_2)_m$—X-phenyl-C(O)O$R_6$, m is an integer in the range of 1–4, X is O or $CH_2$, and $R_6$ is $C_1$–$C_4$alkyl, to form a compound of formula (IV)

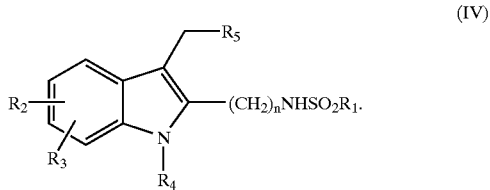
(IV)

12. The process of claim 11 wherein the aldehyde compound is reacted in a solution comprising triethylsilane, trifluoroacetic acid and water.

13. The process of claim 11 further comprising converting the compound of formula (IV) to a compound of formula (V)

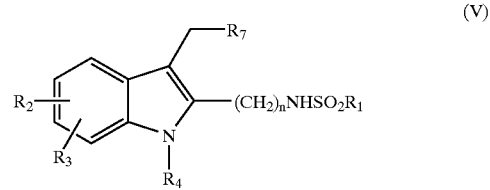
(V)

wherein $R_7$ represents —$(CH_2)_m$—X-phenyl-C(O)OH, m is an integer in the range of 1–4, and X is O or $CH_2$.

14. The process of claim 13 further comprising converting the compound of formula (V) into a pharmaceutically acceptable salt or ester thereof.

15. A product made according to the process of claim 1.

16. A compound selected from the group consisting of:

N-{4-[2-(benzhydrylamino)-5-chlorophenyl]but-3-ynyl}-1-(3,4-dichlorophenyl)-methanesulfonamide.

17. A compound selected from the group consisting of:

N-{4-[2-(benzhydrylamino)-5-chlorophenyl]but-3-ynyl}-1-(2,6-dimethylphenyl)-methanesulfonamide, N-{4-[2-(benzhydrylamino)-5-chlorophenyl]but-3-ynyl}-1-(2-(trifluoromethyl)phenyl)-methanesulfonamide.

18. A compound of formula:

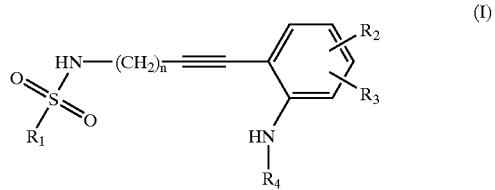
(I)

wherein:

n is an integer in the range of 0–10;

$R_1$ represents a straight or branched $C_1$–$C_{10}$alkyl group or —$CH_2$-phenyl wherein the phenyl optionally has up to two substituents independently selected from the group consisting of $C_1$–$C_4$alkyl, $C_1$–$C_4$alkoxy, halogen, and nitrile, each alkyl and alkoxy being optionally substituted by from one to the maximum number of halogen atoms;

$R_2$ and $R_3$ are each independently selected from the group consisting of H, halogen, nitrile, $C_1$–$C_4$alkyl, and $C_1$–$C_4$alkoxy; and $R_4$ represents a straight or branched $C_1$–$C_{10}$ alkyl group,

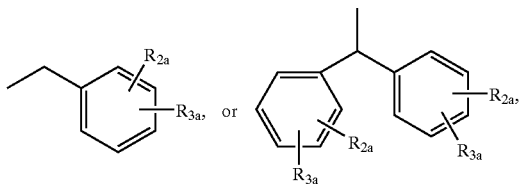

wherein $R_{2a}$ and $R_{3a}$ are each independently selected from the group consisting of H, halogen, nitrile, $C_1$–$C_4$alkyl, and $C_1$–$C_4$alkoxy.

19. A compound according to claim 18 wherein n is an integer in the range of 0–4, $R_1$ represents —$CH_2$-phenyl and the phenyl ring optionally has up to two halogen, alkyl, or perfluoroalkyl substituents, and $R_4$ is a benzhydryl group.

20. A compound according to claim 18 represented by the formula

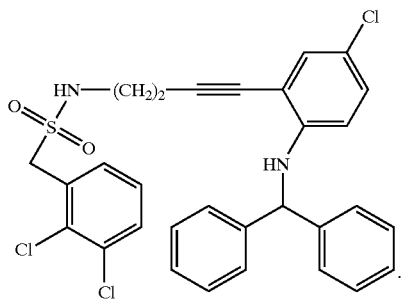

* * * * *